United States Patent [19]

Jeck

[11] 4,360,270
[45] Nov. 23, 1982

[54] CALIBRATION AND TESTING DEVICE FOR OPTICAL, SINGLE PARTICLE, SIZE SPECTROMETERS

[76] Inventor: Richard K. Jeck, 197 W. Paddock Cir., Arnold, Md. 21012

[21] Appl. No.: 234,500

[22] Filed: Feb. 17, 1981

[51] Int. Cl.³ .............................................. G08B 17/10
[52] U.S. Cl. ..................................... 356/243; 356/338
[58] Field of Search .......................... 356/243, 336, 338

[56] References Cited

U.S. PATENT DOCUMENTS 3,868,184 2/1975 Marsocci .............................. 356/338
3,953,128 4/1976 Holly ................................... 356/349
4,135,821 1/1979 Pechiu et al. .................... 356/243 X Primary Examiner—John K. Corbin
Assistant Examiner—Matthew W. Koren
Attorney, Agent, or Firm—Haight & Associates

[57] ABSTRACT

A device comprising a set of fine, uniform, translucent fibers mounted on a suitable holder. When used in conjunction with appropriate neutral density optical filters, if necessary, on suitable particle sizing instruments, the device can easily and quickly be used to perform three important functions—namely, to accurately check the instrument calibration or response to particle size, to locate the limits of the optical depth of field in the particle illuminating beam, and to test the ability of the instrument to detect and register all validly sampled, *single* particle events.

12 Claims, 4 Drawing Figures

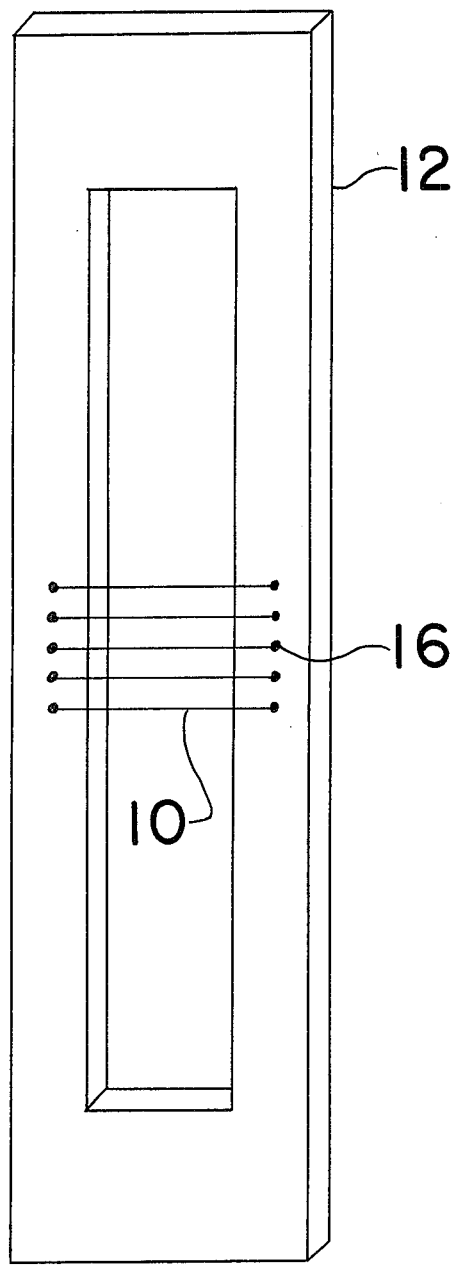
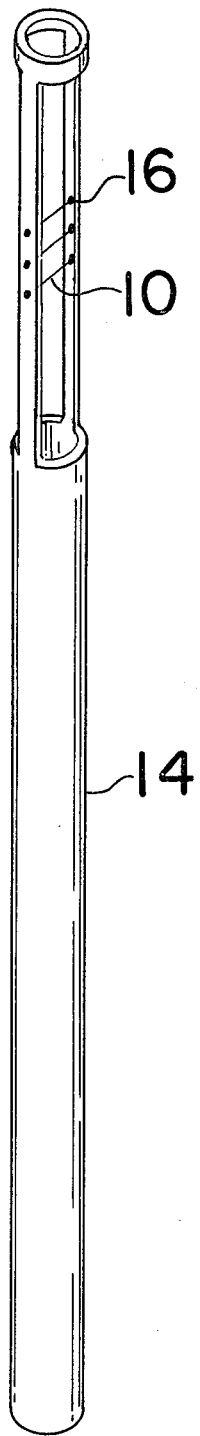
FIG. 1
FIG. 2

CALIBRATION AND TESTING DEVICE FOR OPTICAL, SINGLE PARTICLE, SIZE SPECTROMETERS

BACKGROUND OF THE INVENTION

This invention relates to particle size measuring instruments in general and in particular to devices for checking the calibration, sensitive volume, and particle counting efficiency of optical, single particle size spectrometers.

During the last decade or so, instruments have become commercially available for measuring the size of individual, microscopic, airborne particles such as cloud droplets or other particulate aerosols. These instruments, called particle size spectrometers, are generally based on the principle of visible light scattering by particles aspirated through an illuminating beam. For particles larger than about 20 $\mu$m diameter some spectrometers are based on light interception or shadow imaging techniques.

In the light-scattering models, light scattered out of the illuminating beam by passing aerosol particles is collected by a mirror or lens and directed to a sensitive photodetector. The photodetector current pulses are amplified and, by means of electronic pulse height analysis techniques, they are sorted and counted in histogram form. The number of counts indicates the particle concentration and the histogram provides a size frequency distribution for the detected particles. A given spectrometer will respond to particles within some preselected interval of sizes, such as 1 to 30 $\mu$m diameter, for example. The histogram readout further divides this interval typically into five to fifteen sub intervals or size categories.

A problem common to all such spectrometers is the need for calibration so that the instrument will properly indicate the size of each validly sampled particle. A good primary calibration requires so much care and special equipment that practically all instrument users rely on the manufacturers to provide such services. For spectrometers sensitive to particles larger than about 10 $\mu$m diameter, a rough calibration can be performed in the field with the use of commercially available, microscopic glass beads. However, the available beads are sufficiently varied in size within a sample that the finer size resolution capabilities of some instruments cannot be properly tested.

Related, important problems include the need for measuring the optical depth of field (the length of that portion of the illuminating beam which is sensitive to transiting particles) and the efficiency of the instrument in registering every validly sampled particle.

The prior art for accomplishing these objectives is described below, along with the disadvantages inherent in the prior art.

a. Primary Calibrations

A primary calibration basically consists of adjusting amplifier gains and or noting the size categories into which appear particle counts from a sample of known, uniform (monodisperse) sized particles of the type to be measured in application. By selectively changing the monodisperse size of the test particles, the total instrument response (a determination of the particle diameters corresponding to each of the available size categories for the instrument) can be obtained.

The principal difficulties involved here are in the production of test particles of a known and stable, monodisperse size. For most common applications water droplets would be the preferred test particles but monodisperse droplets are difficult to produce in the diameter range of 0.1 to 10 $\mu$m covered by a majority of the optical, single particle spectrometers in use. Even if a reasonable monodispersity can be initially achieved by some type of droplet generator, it is difficult to prevent droplets of this small size from evaporating partially during the transit from the generator to the sensitive volume of the particle sizing instrument.

To avoid these difficulties, various types of microscopic latex spheres, oil droplets, or other non volatile particles are generally used. However, the special equipment (nebulizers, air pumps, drying chambers, etc.) required is sufficiently elaborate and the procedures sufficiently tedious that most instrument owners rely upon the manufacturers to provide this primary calibration service. Such equipment is definitely impractical for routine use in the field.

The only existing method that is simple enough for use in the field involves the use of microscopic glass spheres or "beads." These are commercially available but are not very practical in sizes smaller than the nominal 13 $\mu$m diameter size class produced by the principal manufacturer. The available sizes are not very monodisperse either, with the result that the range of bead diameters is wider than the resolution capabilities of some instruments. Other difficulties with the glass bead method are:

First, the test results are generally not as reproducible as is desired for an accurate calibration check.

Second, for instruments not equipped with an internal blower or pump for pulling sample air through the sensor unit, extra blowers, pumps, connecting tubes and fittings are necessary for preparing the probe for the calibration checks.

Third, since the microscopic beads have the consistency of a fine powder which almost floats in the air, the procedure must usually take place inside a room or other shelter that is free from drafts or air currents that interfere with the dispensing and use of the beads, and thus, Fourth, the procedure usually requires dismounting the probe from its normal outdoor sampling location (ship, tower, aircraft, roof, etc.), carrying it inside along with its power and data cables or some auxiliary set of cables, and generally proceeding through an annoying, if not difficult, exercise.

For the beam attenuation or shadow imaging type of particle size spectrometers a calibration technique involving the use of opaque wires has recently been disclosed in U.S. Pat. No. 4,135,821 entitled "CALIBRATION OF OPTICAL PARTICLE SIZE ANALYZER" issued in the names of applicants William H. Pechin, Louis H. Thacker, and Lloyd J. Turner. It must be pointed out here that the translucent fibers of the present invention are suitable for use with these types of analyzers as well as with the light-scattering types, but the opaque wires are not. That is, translucent fibers of an adequate diameter will cast a measuring shadow as will opaque wires, but the latter will not scatter light in a way that is uniquely related to the wire diameter. Light-scattering spectrometers are designed to measure the intensity of light deflected out of the beam, usually in a near forward direction, by passing particles. For the microscopic particles of interest, this deflection is due to both scattering and refraction by the translucent particles. The resultant deflected intensity is a unique function of the particle diameter, index of refraction, wavelength of the light in the illuminating beam, and the angle of deflection. Opaque objects can only reflect and/or absorb the illuminating beam, and the reflection mechanism does not deflect light in a way that is unambiguously related to the diameter of the object.

For these reasons it is to be further emphasized that the invention of an opaque wire technique for performing primary calibrations on beam attenuating type analyzers does not imply the use of translucent fibers as an obvious technique for calibrating light-scattering spectrometers. The latter are based on the teachings of light-scattering theory as applied to spherical particles. The theory is very complex, mathematically, even when applied to this simplest of symmetries—the sphere. Non-spherical particles not only enormously complicate the mathematics of the theory but are also unsuitable for use with existing particle size spectrometers. This is because the intensity of light scattered into the detector by non-spherical particles depends on the shape of the particle and on the angle the particle symmetry axes make with the illuminating beam as the particle passes through. Since this angle is generally random there is no longer a unique relationship between the detected light signal and the size of the particle as there is for spherical particles. Fortunately, many of the naturally occurring particles of interest are spherical in shape. Thus, those skilled in the art of light-scattering particle size spectrometry have logically chosen spherical test particles for use in the calibration and testing of these instruments. Calibration tests have therefore been thought of only in terms of primary calibrations since the test particles were of the same size and shape as the particles to be measured in applications. Until the disclosure of this present invention, it was apparently not realized that aligned, translucent, cylindrical fibers could be used in place of microscopic spheres, not as primary calibration particles but as secondary, or transfer standards for checking or adjusting the calibration once a primary calibration with translucent, microscopic spheres had been performed.

b. Determination of the Optical Depth of Field

In addition to accurate particle size determination, practical use of the data obtained with these instruments requires a knowledge of the particle number density—the number of particles per unit volume of the sampled air. This information is easily available if the air samples are aspirated through the probe at a known flow rate and if the sensitive volume of the illuminating beam is known. The sensitive volume is simply the product of the effective beam width and the depth of field (d.o.f.) determined by the imaging optics and the detection system in the instrument. The d.o.f. is preset by the manufacturer but since it may be defined and controlled by optical and electronic components it is subject to change if these components change or drift.

The prior art for measuring or checking the position and length of the d.o.f. involves the insertion of a suitable, usually static, test object in the particle illuminating beam while an electrical or optical response somewhere in the instrument is monitored. The disadvantages of the prior art are:

First, the particle analyzer must usually be opened up to measure voltages on electronic circuits that are normally inaccessible, and therefore, Second, the probe must usually be dismounted from its normal, outdoor sampling location as in the case of prime calibration checks.

Third, the measurements usually require an oscilloscope or other laboratory instruments which therefore make field checks less practical.

c. Efficiency Checks of Particle Counting Circuitry

It is not unusual that during extended field deployments of optical particle counters the indicated particle counts may sometimes decrease significantly without any apparent reason. Sometimes this decrease is a natural result of unusual atmospheric conditions, for example, but it can also be due to instrument malfunction.

There is no known prior art that is capable of providing an exactly countable sequence of individual test particles with diameters less than about 100 $\mu$m for testing the counting efficiency of optical scattering spectrometers.

BRIEF SUMMARY OF THE INVENTION

The general purpose of this invention is to provide a single, quick and reliable calibration checking device for use with optical, single particle, size spectrometers.

Accordingly, it is an object of this invention to provide a repeatable sequence of scattered light pulses or shadow images for use in adjusting the spectrometer calibration or for detecting any change or drift in calibration of said spectrometers.

Another object is to provide a simple, easily used calibration standard for field adjustment of the spectrometer calibration.

A further object of the invention is to provide a simple, easily used method for locating and measuring the limits of the optical depth of field in the sensitive volume of the particle illuminating beam in suitable spectrometers.

Still another object is to provide a reliable means for testing the efficiency of these spectrometers in detecting and counting *single* particle events.

These and other objects and advantages of the invention will appear more fully from consideration of the detailed description, which follows, in conjunction with the accompanying drawing wherein two embodiments of the invention are illustrated. It is to be expressly understood, however, that the drawing is for the purposes of illustration and description and is not to be construed as defining the limits of the invention.

BRIEF DESCRIPTION OF THE DRAWING

FIG. 1 is a view in perspective of an embodiment of the invention suitable for use with the ASSP and FSSP models of particle size spectrometers manufactured by Particle Measuring Systems (PMS), Inc., of Boulder, Colo.

FIG. 2 is a view in perspective of an embodiment of the invention suitable for use with the model 241 optical particle counters manufactured by Royco Instruments Co. of Menlo Park, Calif.

DETAILED DESCRIPTION OF THE INVENTION

FIGS. 1 and 2 show two embodiments of the invention which, basically, has two parts. First there is a set of one or more uniform, translucent fibers 10 which serve as substitute test particles. Second, there is a frame 12, 14 for holding the fibers in place across an unobscured opening. Frame 12, 14 need not entirely enclose the unobstructed opening but may instead be bounded on three sides (U-shaped), or two sides (V-shaped), or gapped (C-shaped), etc.

The fibers 10 may be nylon, glass, or any other natural or synthetic material, and may be clear, colorless, or colored. A primary requirement is that the optical scattering properties of the fiber must be uniform along the length that is to be exposed to the illuminating beam. The fibers should also be sufficiently thin or otherwise chosen so that the optical signal resulting from their introduction into the light beam is within the intensity range of the detection system for the instrument in use. This intensity limitation may be overcome, however, by attenuating excessively intense optical signals with neutral density filters placed appropriately in the light beam.

Suitable fibers are conveniently obtained from small diameter nylon rope or dental floss, for example. A single fiber from one of these sources may be as narrow as 20 $\mu$m in diameter. One or more of these fibers, with the same or different diameters as desired, may then be positioned across the opening in the holder 12, 14 and secured in place with a dot 16 of model cement or other suitable means of securing.

The dimensions and shape of the holder are determined mainly by the dimensions and shape of the sample inlet orifice of the particle sizing probe in use. Typical outside dimensions are about one by four inches for the embodiment of FIG. 1, and about one eighth by six inches for the embodiment of FIG. 2.

Figure 3:
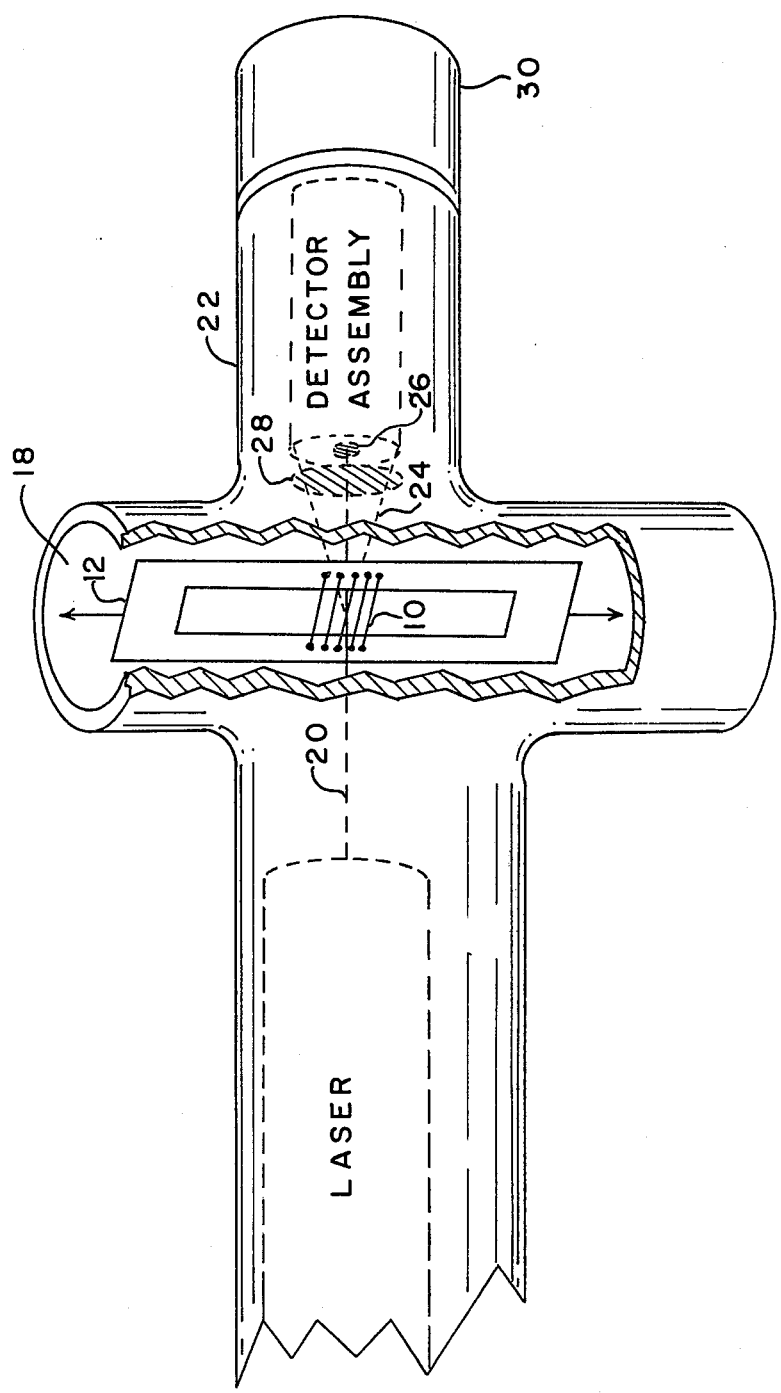
FIG. 3 is a diagrammatic illustration of the optical system of a PMS model ASSP probe with an embodiment of the invention shown in situ in the sampling volume of the illuminating beam.

In FIG. 3 the embodiment of FIG. 1 is shown in situ in the sampling chamber 18 of the PMS model ASSP spectrometer probe 22 shown partially cutaway. The embodiment is shown positioned such that one of the fibers is within the sensitive length of the illuminating laser beam 20. This fiber scatters light in all directions and the detector assembly collects the portion of scattered light that is contained within the solid cone 24 subtended at the intersection of the fiber and the laser beam. The probe manufacturer uses a beam stop 26 to prevent the direct laser beam from entering the detector.

Proper usage of the invention simply requires that the holder 12 be moved within the sampling chamber 18 so that the fibers 10 cross the beam 20 within the sensitive length of said beam. This is easily accomplished by gripping one end of the holder with the thumb and forefinger, or with a suitably long clamp, tong, or plier, and pushing or pulling the holder parallel to the length of the sampling chamber so that the fiber(s) pass(es) one or more times, as desired, through the beam.

The holder 12 may be of any convenient length, but one that is at least two or three inches long has the advantage of allowing a long enough opening that the fibers may be attached to the holder an inch or more from either end of said opening. This configuration makes it easier for the user to move the fibers through the beam and stop the motion of the holder before the edge of said holder reaches the beam. This avoids possible complications from spurious reflections off the end of the holder.

As has been previously indicated, some fibers may require the use of an optical neutral density filter to reduce the intensity of light scattered by the fibers into the detector. Such a filter 28 is shown located in one possible position just ahead of the detector assembly in FIG. 3. This location is convenient since said filter may easily be placed on the front end of the detector assembly by unscrewing cap 30 on the end of probe housing 22 and sliding the detector assembly out of the probe.

The minimum speed with which the fibers must be passed through the laser beam can be determined by trial, but generally said speed is comfortably within the capability of manual movements. About ten centimeters per second is typical.

Finally, the ASSP models generally contain an electronic "velocity reject" feature which must be disabled before the test fibers 10 will be reliably counted. This "velocity reject" feature is designed by the manufacturer to discriminate against particles which just graze the edge of the laser beam during their passage through the sampling chamber 18. In effect, signal voltage pulses from the detector that are narrower than a running average are rejected by the counting circuitry, since said narrower pulses are normally those arising from beam grazing particles. Unfortunately, this "velocity reject" feature will also discriminate against signals from those test fibers of the invention which pass through the beam at a rate faster than the average. Since the speed of travel of the fibers is difficult to control, as the invention is normally manipulated manually, it is better to disable the "velocity reject" circuitry so that all fibers passing through the sensitive length of the beam will be counted. Such temporary disablement capability is easily incorporated into the probe electronics by the simple addition of a switch in an appropriate part of the circuitry as reference to the probe owner's manual will show.

Figure 4:
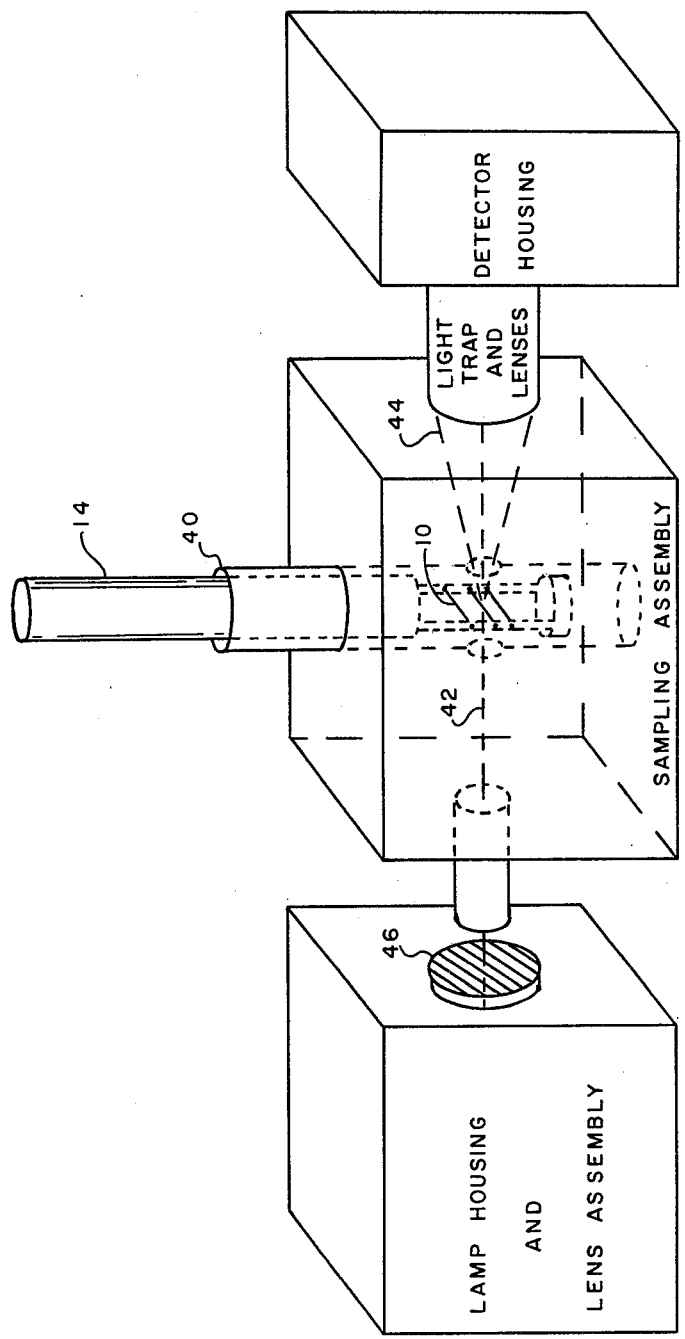
FIG. 4 is a diagrammatic illustration of the optical system of a Royco model 241 particle counter with an embodiment of the invention shown in situ in the sampling volume of the illuminating beam.

In FIG. 4 the embodiment of FIG. 2 is shown in situ in the sampling chamber 40 of the Royco model 241 particle counter partially shown in a schematic view. In the actual instrument the assemblies shown are all enclosed inside a light tight container (not shown). The embodiment is shown positioned such that one of the fibers 10 is within the sensitive volume of the illuminating beam 42. This fiber scatters light in all directions and the detector lens assembly collects the portion of scattered light that is contained within the solid cone 44 subtended at the intersection of the fiber and the illuminating beam. The probe manufacturer uses a light trap to prevent the direct illuminating beam from entering the detector.

Proper usage of the beam simply requires that the holder 14 be moved lengthwise in the sampling chamber 40 so that the fibers 10 cross said illuminating beam one or more times, as desired. This is easily accomplished by grasping the end of the holder 14 that protrudes from the sampling chamber 40 and moving the holder with a push-pull motion.

Some fibers may require the use of an optical neutral density filter to reduce the intensity of light scattered by the fibers into the detector. Such a filter 46 is shown conveniently located in a gap just outside the lamp housing and lens assembly. This location is easily accessible by removing the cover to the light-tight container which houses these assemblies.

The minimum speed with which the fibers must be passed through the illuminating beam can be determined by trial, but said speed is comfortably within the capability of manual movements. About ten centimeters per second is typical.

It should be understood, of course, that the foregoing disclosure relates to only two possible embodients of the invention and that numerous modifications or alterations may be made therein, as suits the application, without departing from the spirit and scope of the invention as set forth in the appended claims. It should also be understood that the invention relates in general to all single particle optical scattering spectrometer type instruments and not to just the two models for which the present embodiments were designed. In addition, the invention relates as well to single particle size spectrometers based on the principle of beam attenuation or shadow imaging techniques in the same way as the opaque wire method of calibration.

The invention may be used in the following ways:

a. Instrument Calibration

The present invention will not normally be used for primary calibrations since the shape and size of the test fibers are completely different from the particles (cloud droplets, smoke, powders, or other aerosols, for example, that are normally measured by these instruments. However, a given test fiber will produce an optical signal of fixed, repeatable amplitude each time the fiber is passed through the sensitive volume of the particle illuminating beam. The fiber will thus simulate a particle event which will be registered in the data readout system of the instrument as a "count" corresponding to some, perhaps originally undetermined, particle size. If the instrument is in proper calibration when the response to one or more test fibers is first documented, then the test fiber(s) will serve as an accurate *transfer standard* for future calibration checks and adjustments.

In succeeding calibration checks the operator simply passes the fiber(s) across the sensitive volume of the particle illuminating beam and observes in the readout the "counts" indicated for the various particle size categories of the instrument. If the counts are distributed among the size categories in a way that is identical to the distribution that was documented when the instrument was known to be properly calibrated by other means, then it will have been demonstrated that the instrument is still in calibration.

If an optical filter is needed to reduce the scattered light intensity, said filter is chosen with an appropriate attenuation factor such that the instrument registers each test signal as a count in one of the available size categories. In such cases, the same optical filter must be used whenever the present invention is used in order to ensure that the net effect will be the same.

b. Measuring the Depth of Field

The present invention may be easily used to locate and measure the optical depth of field (d.o.f.) in the particle illuminating beam of suitable instruments. Basically, the operator simply passes the fibers across the beam at various positions along the length of the beam in the sampling volume of the instrument while observing the instrument readout for an indication of "particle" counts. Within the d.o.f., each test fiber will be counted as a valid particle event as the fiber passes across the beam. When the fibers cross the beam at location outside the d.o.f., no particle counts will be registered. Depending on the accuracy desired, the operator may use a jig or positioning device to obtain more precision in locating the points of passage of the test fibers across the beam.

c. Performance Checks of the Particle Detection and "Single Particle" Counting Capabilities of the Instrument The use of the invention for this application is straight forward. The operator simply passes the fibers across the illuminating beam within the d.o.f. and observes the instrument readout for an indication of one "particle" count for each fiber crossing the beam.

From the foregoing description, one skilled in the art can easily ascertain the essential characteristics of this invention and, without departing from the spirit and scope thereof, can make various changes and modifications of the invention to adapt it to various usages and conditions.

I claim:

1. A calibration device for single particle size spectrometers of the type wherein particles to be measured are directed through a sampling chamber to pass transversely through a portion of a collimated light beam, and wherein light scattered or intercepted by the particles is determined by a detector which provides an indication of the sizes and/or number of said measured particles, said calibration device comprising:

a frame defining an unobstructed opening which is larger than the cross-section of said portion of said light beam;

at least one translucent fiber having at least one lengthwise section with uniform light scattering properties, said lengthwise section being at least as long as the width of said portion of said light beam; and means for securing said fiber to said frame such that said lengthwise section of said fiber is extended across at least part of said unobstructed opening;

wherein said frame is sized to permit it to be moved through the spectrometer sampling chamber while passing said lengthwise fiber section transversely across said portion of said light beam.

2. The calibration device according to claim 1 further comprising at least one additional translucent fiber having a lengthwise section with uniform light scattering properties, and means for securing said additional fiber to said frame such that at least one fiber and said additional fiber are extended in spaced, nominally parallel relation across at least said part of said unobstructed opening.

3. The calibration device according to claim 1 further comprising a plurality of additional translucent fibers having respective lengthwise sections with uniform light scattering properties, and means for securing said additional fibers to said frame such that their lengthwise sections are extended in spaced, nominally parallel relation to each other and to the lengthwise section of said one fiber across said part of said unobstructed opening.

4. The calibration device according to claim 1, wherein said frame is generally rectangular and said unobstructed opening is generally rectangular.

5. The calibration device according to claim 1, wherein said unobstructed opening is generally rectangular.

6. The calibration device according to claim 1, 2, or 3 further comprising handle means secured to and extending from said frame for facilitating movement of said frame in said sampling chamber.

7. The calibration device according to claim 1 or 3 further comprising neutral density optical filter means disposed in the path of said light beam to reduce the intensity of light received by said detector.

8. The calibration device according to claim 7, wherein said filter means is disposed at a location in said beam upstream of said sampling chamber.

9. The calibration device according to claim 7, wherein said filter means is disposed at a location in front of said detector downstream of said sampling chamber.

10. A method for calibrating single particle size spectrometers of the type wherein particles to be measured are directed through a sampling chamber transversely through a collimated light beam, and wherein light scattered or intercepted by the measured particles is monitored by a detector which provides an indication of the sizes and/or number of said measured particles, said method comprising the step of:

passing at least one translucent fiber, having uniform optical characteristics, transversely through said light beam in said sampling chamber in a direction nominally normal to the fiber length while noting the indication provided by said detector.

11. The method according to claim 10 further comprising the step of passing said fiber through said light beam at different locations along the beam length in said sampling chamber.

12. The method according to claim 10 further comprising the step of passing additional optically uniform translucent fibers through said light beam in sequence.

* * * * *